United States Patent
Yoshida (10) Patent No.: US 9,291,445 B2
(45) Date of Patent: Mar. 22, 2016

(54) OPTICAL COHERENCE TOMOGRAPHIC APPARATUS

(75) Inventor: Hirofumi Yoshida, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 220 days.

(21) Appl. No.: 13/598,767

(22) Filed: Aug. 30, 2012

(65) Prior Publication Data

US 2013/0194581 A1 Aug. 1, 2013

(30) Foreign Application Priority Data

Jan. 26, 2012 (JP) ................................. 2012-014582

(51) Int. Cl.
- G01B 9/02 (2006.01)
- A61B 3/10 (2006.01)
- A61B 3/12 (2006.01)
- G01N 21/47 (2006.01)
- A61B 5/00 (2006.01)

(52) U.S. Cl.
CPC ............ G01B 9/02044 (2013.01); A61B 3/102 (2013.01); A61B 3/1225 (2013.01); G01B 9/0203 (2013.01); G01B 9/02091 (2013.01); G01N 21/4795 (2013.01); A61B 5/0066 (2013.01); G01B 2290/65 (2013.01)

(58) Field of Classification Search
CPC .... G01B 9/0203; G01B 9/02091; A61B 3/12; G01N 21/4795
USPC .......................................................... 356/479
See application file for complete search history.

(56) References Cited

U.S. PATENT DOCUMENTS

| 5,537,162 A | 7/1996 | Hellmuth et al. |
| 5,973,781 A | 10/1999 | Moeller et al. |
| 7,980,696 B1 | 7/2011 | Taki et al. |
| 8,098,278 B2 | 1/2012 | Yumikake et al. |

(Continued)

FOREIGN PATENT DOCUMENTS

| CN | 101677761 A | 3/2010 |
| EP | 2 497 409 A1 | 9/2012 |

(Continued)

OTHER PUBLICATIONS

May 21, 2013 European Search Report in European Patent Appln. No. 13000274.4.

(Continued)

*Primary Examiner* — Jonathan Hansen (74) *Attorney, Agent, or Firm* — Fitzpatrick, Cella, Harper & Scinto (57) ABSTRACT

An optical coherence tomographic apparatus which obtains a tomographic image of an object based on light obtained by combining return light from the object irradiated with measurement light through a first lens and reference light corresponding to the measurement light, the apparatus comprises a scanning unit provided on an optical path of the measurement light and configured to scan the measurement light on the object; a second lens disposed between the scanning unit and the object; an optical path branching unit disposed between the first lens and the second lens and configured to make the optical path of the measurement light branch off to an observation optical path for observation of the object; a dividing unit that splits light emitted from a light source into the measurement light and the reference light; and a focus lens disposed between the dividing and scanning units.

24 Claims, 5 Drawing Sheets

(56) References Cited

U.S. PATENT DOCUMENTS

| | | |
|---|---|---|
| 8,294,901 B2 | 10/2012 | Yoshida et al. |
| 8,308,297 B2 | 11/2012 | Hirose et al. |
| 8,403,482 B2 | 3/2013 | Nouchi et al. |
| 2005/0203422 A1 | 9/2005 | Wei |
| 2005/0286019 A1 | 12/2005 | Wiltberger et al. |
| 2010/0110376 A1 | 5/2010 | Everett et al. |
| 2010/0118132 A1 | 5/2010 | Yumikake et al. |
| 2010/0182567 A1 | 7/2010 | Nouchi et al. |
| 2010/0302508 A1 | 12/2010 | Yamamoto et al. |
| 2011/0176107 A1 | 7/2011 | Yoshida et al. |
| 2011/0299037 A1 | 12/2011 | Ueno |
| 2012/0250029 A1 | 10/2012 | Yoshida |

FOREIGN PATENT DOCUMENTS

| | | |
|---|---|---|
| JP | 10-262929 A | 10/1998 |
| JP | 2008-289643 A | 12/2008 |
| JP | 2010-197180 A | 9/2010 |
| JP | 2011-011052 A | 1/2011 |
| JP | 2011-147612 A | 8/2011 |
| JP | 2011-212432 A | 10/2011 |
| WO | 2010/074279 A1 | 7/2010 |
| WO | 2011/077634 A1 | 6/2011 |

OTHER PUBLICATIONS

Jul. 3, 2014 Chinese Official Action in Chinese Patent Appln. No. 201310030480.1.

Jun. 24, 2014 Russian Official Action in Russian Patent Appln. No. 2013103488.

OPTICAL COHERENCE TOMOGRAPHIC APPARATUS

BACKGROUND OF THE INVENTION

1. Field of the Invention

The present invention relates to an optical coherence tomographic apparatus, for example, an optical coherence tomographic apparatus which is used for ophthalmic care and the like.

2. Description of the Related Art

Currently, various ophthalmic apparatuses using optical apparatuses are known. For example, various apparatuses such as an anterior ocular segment imaging apparatus, fundus camera, and SLO (Scanning Laser Ophtalmoscope) are used as optical apparatuses for the observation of an eye to be examined. Among these apparatuses, an optical coherence tomographic apparatus based on OCT (Optical Coherence Tomography) using multiwavelength light wave coherence can obtain a tomographic image of a sample at high resolution. The apparatus is becoming indispensable to outpatient clinics specialized in retinas as an ophthalmic apparatus. This apparatus will be referred to as an OCT apparatus hereinafter.

An OCT apparatus irradiates a sample with measurement light which is low-coherent light, and can perform high-sensitivity measurement of backscattered light from the sample by using an interference system or interference optical system. Low-coherent light has the property of being able to obtain a high-resolution tomographic image by increasing the wavelength width. In addition, the OCT apparatus can obtain a high-resolution tomographic image by scanning measurement light on a sample. Therefore, the OCT apparatus can obtain a tomographic image of the retina at the fundus of an eye to be examined, and hence has been widely used for ophthalmic care and the like for the retina.

On the other hand, the OCT apparatus as an ophthalmic apparatus is generally equipped with optical systems for fundus observation, anterior eye observation, and the like to implement alignment adjustment between the apparatus and an object to be examined. In order to use the OCT apparatus together with these optical systems, the apparatus is configured to use light of different wavelengths for the respective optical systems and perform wavelength separation by using a wavelength separation unit such as a dichroic mirror. However, since low-coherence light having a wavelength width is used for the OCT apparatus, it is difficult to separate the wavelength of light used by an optical system for fundus observation, anterior eye observation, or the like from the wavelength of light used by the OCT apparatus.

According to U.S. Pat. No. 5,537,162, a beam scanner position is set on the back focal plane of a lens to make the incident angles of beams on dichroic mirrors constant even when performing beam scanning. This can unify the characteristics of the dichroic mirrors and increase the accuracy of wavelength separation.

According to U.S. Pat. No. 5,537,162, however, when performing focus adjustment for the fundus of an eye to be examined, the beam scanner and the lens are driven together. The lens having the back focal plane disposed on the beam scanner tends to increase in size to capture scan light from the beam scanner. It is therefore necessary to move the beam scanner together with the large lens. This increases the complexity of the driving mechanism. In addition, since they are moved together, it is necessary to simultaneously move a measurement light source optically conjugate to the fundus position. If this measurement light source is placed on an optical fiber end, it is necessary to move the optical fiber. This may change the polarization state.

SUMMARY OF THE INVENTION

In consideration of the above problems, the present invention provides an optical coherence tomographic apparatus which can simplify a driving mechanism and reduce a change in polarization state due to the movement and the like of a measurement light source.

According to one aspect of the present invention, there is provided an optical coherence tomographic apparatus which obtains a tomographic image of an object based on light obtained by combining return light from the object irradiated with measurement light through a first lens and reference light corresponding to the measurement light, the apparatus comprising: a scanning unit configured to be provided on an optical path of the measurement light and configured to scan the measurement light on the object; a second lens configured to be disposed between the scanning unit and the object on the optical path of the measurement light; an optical path branching unit configured to be disposed between the first lens and the second lens and configured to make the optical path of the measurement light branch off to an observation optical path for observation of the object; a dividing unit configured to split light emitted from a light source into the measurement light and the reference light; and a focus lens configured to be disposed between the dividing unit and the scanning unit on the optical path of the measurement light.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

This embodiment will be described below with reference to the accompanying drawings. Note that the same reference numerals throughout the specification denote the same constituent elements.

(First Embodiment: OCT Optical System)
<Apparatus Arrangement>

Figure 1:
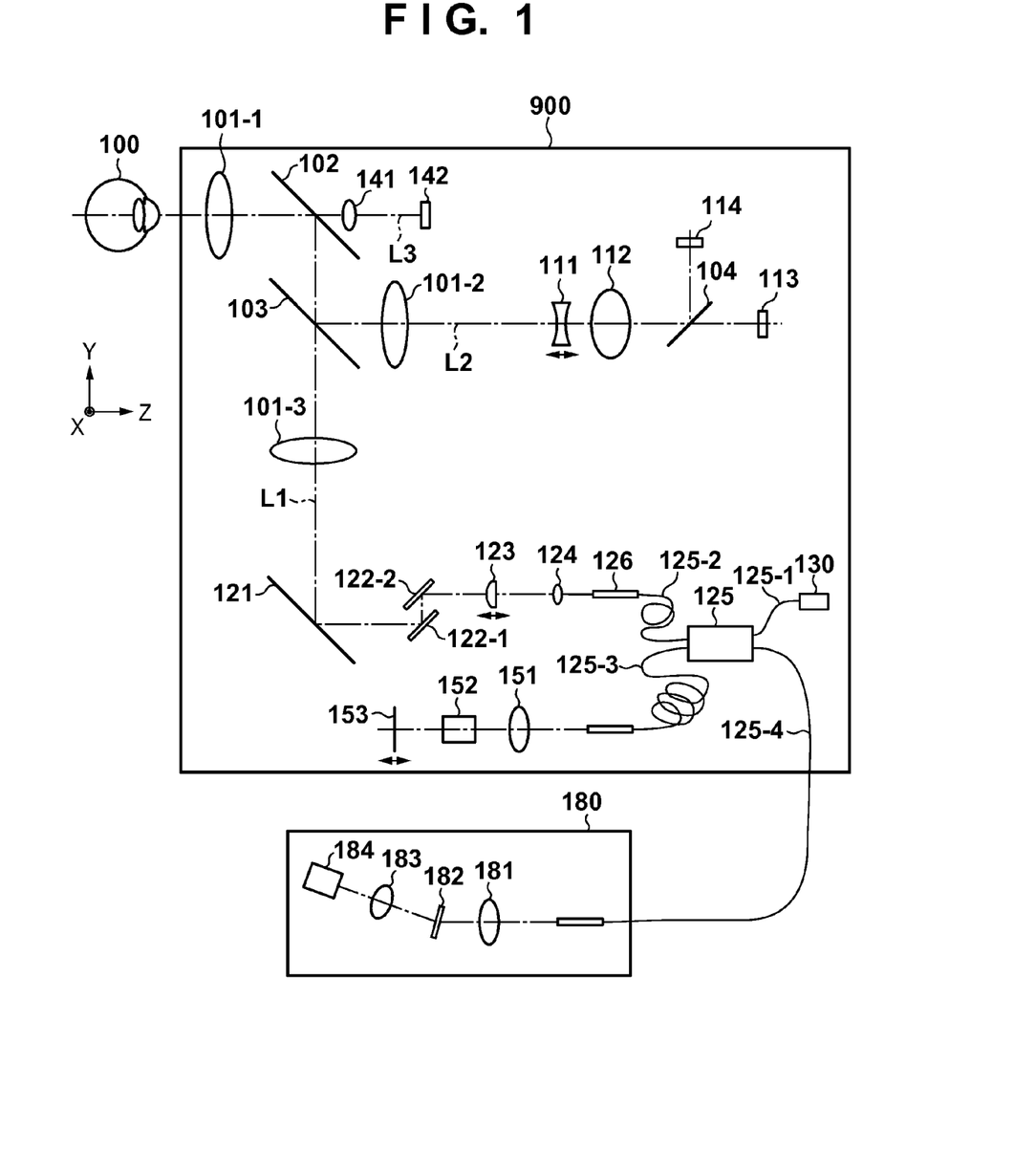
FIG. 1 is a view showing the schematic arrangement of an optical coherence tomographic apparatus according to the first embodiment.

The arrangement of an optical coherence tomographic apparatus (OCT apparatus) according to the first embodiment will be described with reference to FIG. 1. The optical coherence tomographic apparatus includes an optical head 900 and a spectrometer 180. The optical coherence tomographic apparatus obtains a tomographic image of an object to be examined based on the light obtained by combining return light from the object irradiated with measurement light through a scanning unit and reference light corresponding to the measurement light.

The internal arrangement of the optical head 900 will be described first. The optical head 900 is formed by a measurement optical system for capturing an anterior eye image of an eye 100 to be examined and a two-dimensional image and tomographic image of the fundus. An objective lens 101-1 is disposed to face the eye 100. On the optical axis of this lens, a first dichroic mirror 102 and a second dichroic mirror 103, which serve as optical path branching units, split the optical path. That is, they split the optical path for each wavelength band into a measurement optical path L1 of an OCT optical system, a fundus observation optical path/fixation lamp optical path L2, and an anterior ocular segment observation optical path L3.

A third dichroic mirror 104 further branches the optical path L2 for each wavelength band into an optical path to a CCD 114 for fundus observation and an optical path to a fixation lamp 113. In this case, of lenses 101-2, 111, and 112, the lens 111 is driven by a motor (not shown) for focus adjustment for a fixation lamp and fundus observation. The CCD 114 has sensitivity near the wavelength of fundus observation illumination light (not shown), more specifically, 780 nm. On the other hand, the fixation lamp 113 generates visible light to urge the object to fix the vision. A lens 141 and an infrared CCD 142 for anterior eye observation are disposed on the optical path L3. The infrared CCD 142 has sensitivity near the wavelength of anterior eye observation illumination light (not shown), more specifically, 970 nm.

The optical path L1 forms an OCT optical system, as described above, and is used to capture a tomographic image of the fundus of the eye 100. More specifically, this optical path is used to obtain an interference light for forming a tomographic image. A lens 101-3, a mirror 121, and an X scanner 122-1 (first scanning unit) and Y scanner 122-2 (second scanning unit) which serve as scanning units are disposed on the optical path L1. The X scanner 122-1 and Y scanner 122-2 scan light on the fundus of the eye 100 in the X direction (main scanning direction) as an example of the first direction and the Y direction (sub-scanning direction) as an example of the second direction intersecting the first direction. Note that the optical path between the X scanner 122-1 and the Y scanner 122-2 in FIG. 1 runs in a direction parallel to the drawing surface. In practice, however, this optical path runs in a direction perpendicular to the drawing surface.

Figure 2:
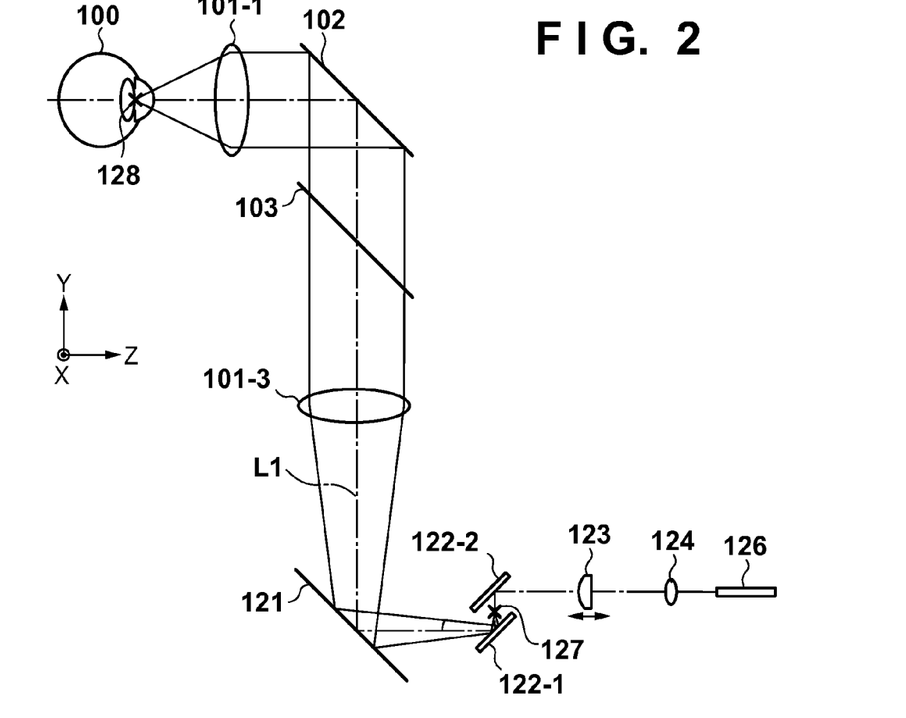
FIG. 2 is a view showing a pupil light beam in the optical coherence tomographic apparatus according to the first embodiment.

The detailed arrangement on the optical path L1, the conjugate relationship between the optical path L1 and the pupil position, and light beams passing through the pupil will be described with reference to FIG. 2. A position conjugate to a predetermined region such as the anterior ocular segment of the eye is located between the first and second scanning units. In this embodiment, a scanner central position 127 between the X scanner 122-1 and the Y scanner 122-2 is conjugate to a pupil position 128 of the eye 100.

The lens 101-1 (first lens), the lens 101-3 (second lens), and the X scanner 122-1 and Y scanner 122-2 (or the scanner central position 127) are disposed so as to make a light beam between the lens 101-1 and the lens 101-3 become almost parallel. According to this arrangement, an optical path with a measurement light deflecting unit serving as an object point becomes almost parallel between the lens 101-1 and the lens 101-3. This can make the incident angle of light on the first dichroic mirror 102 coincide with that on the second dichroic mirror 103, even when the X scanner 122-1 and the Y scanner 122-2 perform scanning.

A measurement light source 126 is a light source for measurement light which makes measurement light enter a measurement optical path. In this embodiment, the measurement light source 126 is disposed on a fiber end and optically conjugate to the fundus region of the eye 100. Of lenses 123 and 124, the lens 123 is driven by a motor (not shown) in the directions indicated by a double-headed arrow to perform focus adjustment. Focus adjustment is performed by adjusting light emitted from the measurement light source 126 on the fiber end so as to focus the light on the fundus. The lens 123 as a focus adjustment unit is disposed between the measurement light source 126 and the X scanner 122-1 and Y scanner 122-2 which serve as a measurement light deflecting unit. This makes it unnecessary to use a lens larger than the lens 101-3 or move a fiber 125-2 connected to the measurement light source 126.

This focus adjustment makes it possible to form an image of the measurement light source 126 on the fundus of the eye 100 and to efficiently return return light from the fundus of the eye 100 to the fiber 125-2 through the measurement light source 126.

The arrangements of the optical path of light emitted from a light source 130, reference optical system, and spectrometer 180 in FIG. 1 will be described next. The light source 130, a mirror 153, a dispersion-compensating glass 152, an optical coupler 125, optical fibers 125-1 to 125-4, a lens 151, and the spectrometer 180 constitute a Michelson interferometer system. The optical fibers 125-1 to 125-4 are single-mode optical fibers, which are connected to the optical coupler 125 so as to be integrated.

The light emitted from the light source 130 is split into measurement light which emerges to the optical fiber 125-2 through the optical fiber 125-1 and the optical coupler 125 and reference light which emerges to the optical fiber 125-3. The measurement light enters the fundus of the eye 100 as an observation target through the above OCT optical system optical path and reaches the optical coupler 125 through the same optical path by reflection and scattering by the retina.

On the other hand, reference light reaches and is reflected by the mirror 153 through the optical fiber 125-3, the lens 151, and the dispersion-compensating glass 152 inserted to match the dispersion of measurement light with that of reference light. This light then returns along the same optical path and reaches the optical coupler 125.

The optical coupler 125 combines measurement light and reference light to form interference light. In this case, interference occurs when the optical path length of the measurement light becomes almost equal to that of the reference light. A motor and driving mechanism (not shown) hold the mirror 153 so as to adjust its position in the optical axis direction, thereby matching the optical path length of measurement light, which changes depending on the eye 100, with that of reference light. Interference light is guided to the spectrometer 180 through the optical fiber 125-4.

The spectrometer 180 includes a lens 181, a diffraction grating 182, a lens 183, and a line sensor 184. The interference light emerging from the optical fiber 125-4 is made almost parallel through the lens 181, and then spectroscoped by the diffraction grating 182. The lens 183 forms the light into an image on the line sensor 184.

The light source 130 will be described next. The light source 130 is an SLD (Super Luminescent Diode) which is a typical low-coherent light source. The central wavelength is 855 nm, and the wavelength is about 100 nm. In this case, the wavelength band width is an important parameter which influences the resolution of an obtained tomographic image in the optical axis direction. In addition, an SLD is selected as a light source in this case. However, ASE (Amplified Spontaneous Emission) or the like may be used as long as it can emit low-coherent light. In consideration of measurement of the eye to be examined, the wavelength of infrared light is suitable as the central wavelength to be set. In addition, the central wavelength influences the resolution of an obtained tomographic image in the horizontal direction, and hence is preferably as short as possible. For the two reasons, the central wavelength is set to 855 nm.

Although this embodiment uses a Michelson interferometer as an interferometer, a Mach-Zehnder interferometer may be used. It is preferable to use a Mach-Zehnder interferometer when the light amount difference between measurement light and reference light is large, and a Michelson interferometer when the light amount difference is relatively small.

<Method of Capturing Tomographic Image>

An optical coherence tomographic apparatus can capture a tomographic image of a desired region of the fundus of the eye 100 by controlling the X scanner 122-1 and the Y scanner 122-2.

Figure 3:
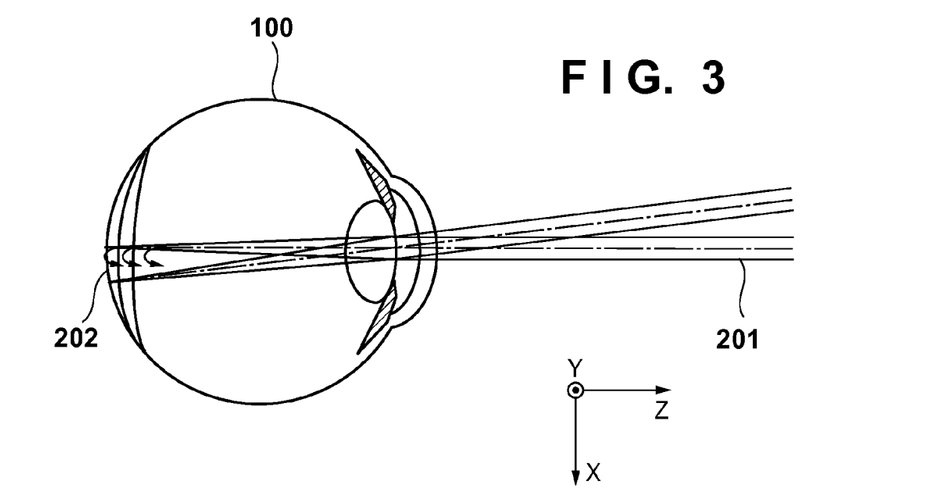
FIG. 3 is a view showing how an eye to be examined is scanned in the x direction.

FIG. 3 shows how the eye 100 is irradiated with measurement light 201 to scan a fundus 202 in the x direction. The line sensor 184 captures information corresponding to a predetermined number of imaging lines from the imaging range on the fundus 202 in the x direction. The luminance distribution on the line sensor 184 which is obtained at a given position in the x direction is FFTed (Fast Fourier Transformed). The image obtained by converting the density or color information of the linear luminance distribution obtained by FFT so as to display it on a monitor will be referred to as an A-scan image. The two-dimensional image obtained by arranging a plurality of A-scan images will be referred to as a B-scan image. It is possible to obtain a plurality of B-scan images by capturing a plurality of A-scan images for forming one B-scan image first, and then performing scanning in the x direction again upon moving the scan position in the y direction. Displaying a plurality of B-scan images or the three-dimensional tomographic image formed from a plurality of B-scan images on the monitor allows the examiner to use the image or images for the diagnosis of the eye.

Figure 4:
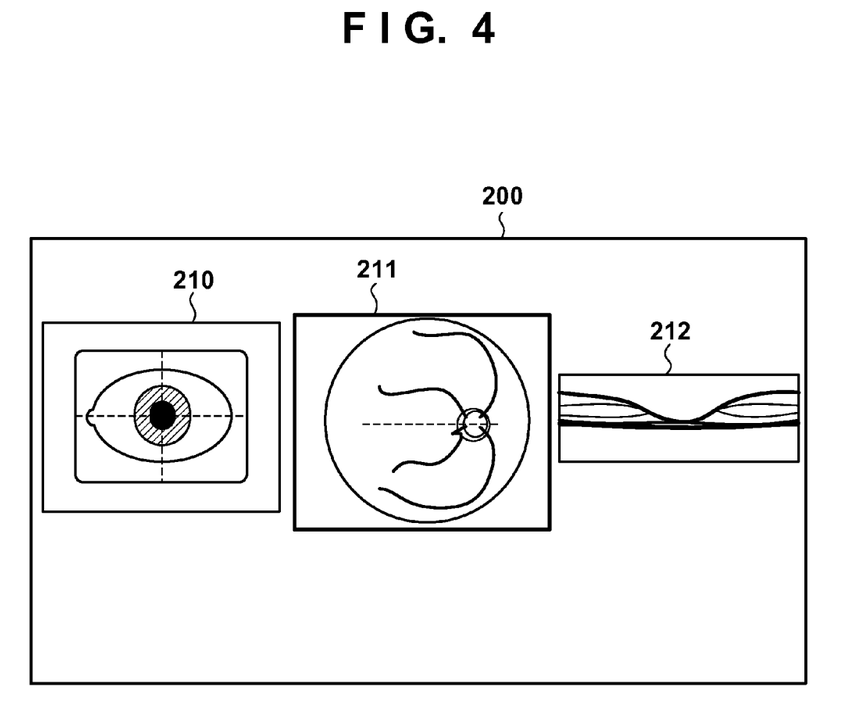
FIG. 4 is a view showing the anterior eye image, two-dimensional fundus image, and B-scan image displayed on a monitor.

FIG. 4 shows an example of an anterior eye image 210, two-dimensional fundus image 211, and B-scan image 212 as a tomographic image displayed on a monitor 200. The anterior eye image 210 is the image which is output from the infrared CCD 142, processed, and displayed. The two-dimensional fundus image 211 is the image which is output from the CCD 114, processed, and displayed. The B-scan image 212 is the image which is output from the line sensor 184 and formed by the above processing.

As described above, according to this embodiment, in the optical coherence tomographic apparatus, a focus adjustment unit (the lens 123 and a driving mechanism (not shown)) for the focus adjustment of the eye is disposed between the measurement light deflecting unit (XY scanner) which deflects measurement light and the measurement light source 126. In addition, the first lens (lens 101-1) and the second lens (lens 101-3) are provided on the measurement optical path between the measurement light deflecting unit (XY scanner) and the eye 100, and the optical path branching unit (the first dichroic mirror 102 and the second dichroic mirror 103) is disposed between the first leans and the second lens.

That is, disposing the focus lens between the measurement light source on the fiber end and the XY scanner which is the measurement light deflecting unit eliminates the necessity to move the optical fiber 125-2 and the like connected to the lens 101-3 and the measurement light source 126. This can simplify the driving mechanism. In addition, since there is no need to move the fiber end, it is possible to provide an optical coherence tomographic apparatus which can keep a polarization state.

In addition, according to this embodiment, in the optical coherence tomographic apparatus, the first lens (lens 101-1), the second lens (lens 101-3), and the measurement light deflecting unit (XY scanner) are disposed upon position adjustment so as to make light parallel on the measurement optical path between the first lens (lens 101-1) and the second lens (lens 101-3). This can make the incident angles of beams on the first and second dichroic mirrors 102 and 103 constant and improve the wavelength separation accuracy.

Although this embodiment has been described on the eye to be examined, it is possible to scan on an object to be examined, other than the eye to be examined, such as the skin or organ. The present invention can be applied to imaging apparatuses such as endoscopes other than ophthalmic apparatuses.

(Second Embodiment: SLO Optical System)
<Apparatus Arrangement>

Figure 5:
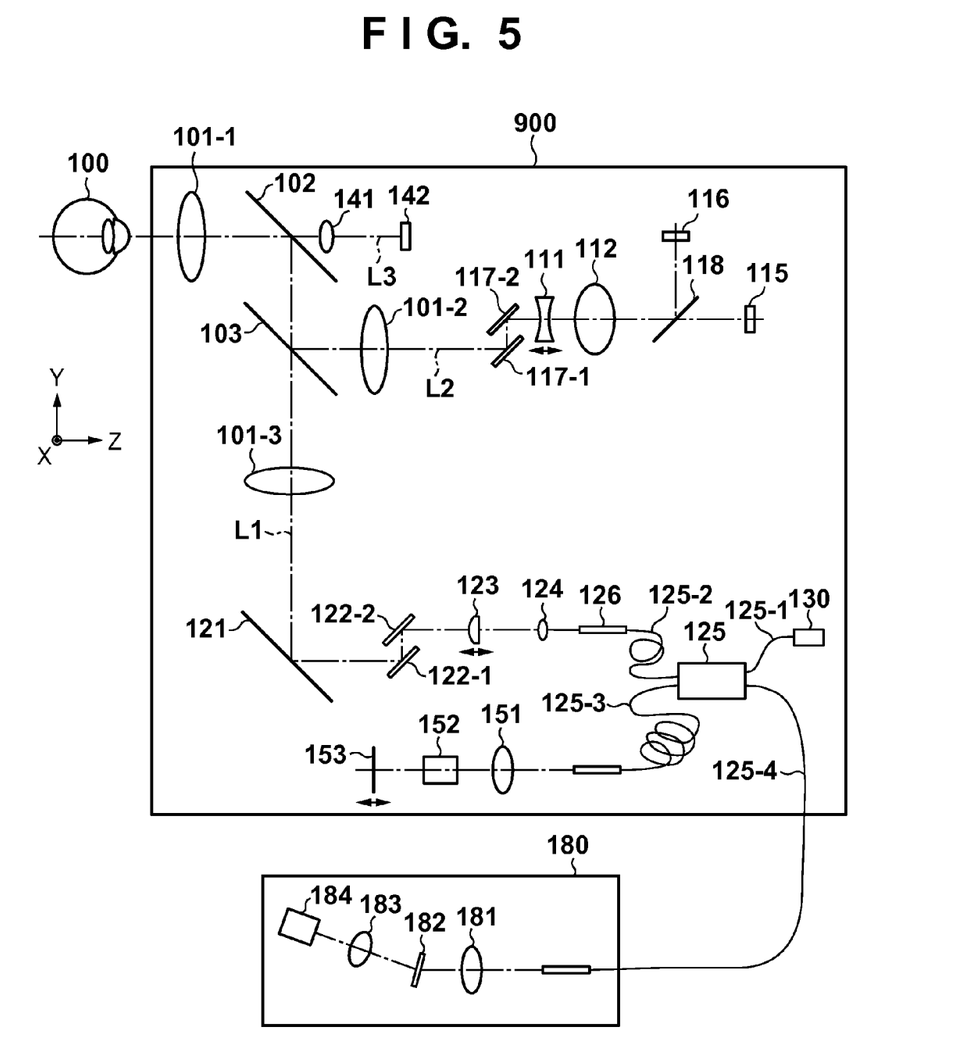
FIG. 5 is a view showing the schematic arrangement of an optical coherence tomographic apparatus according to the second embodiment.

The arrangement of an optical coherence tomographic apparatus (OCT apparatus) according to the second embodiment will be described with reference to FIG. 5. The optical coherence tomographic apparatus includes an optical head 900 and a spectrometer 180 as in the first embodiment.

In the first embodiment, the optical path L2 is formed to make the CCD 114 for fundus observation obtain a two-dimensional fundus image of the eye 100. In contrast to this, in the second embodiment, an X scanner and a Y scanner are disposed on an optical path L2, and the optical path L2 is formed to obtain a two-dimensional fundus image by scanning a spot on the fundus. The arrangements on optical paths L1 and L3 and the arrangement of a spectrometer 180 are the same as those in the first embodiment, and hence a description of them will be omitted.

The arrangement on the optical path L2, which differs from that in the first embodiment, will be mainly described below. Lenses 101-2, 111, and 112 are the same as those in the first embodiment. A motor (not shown) for focus adjustment for fundus observation drives the lens 111. A light source 115 generates light having a wavelength of 780 nm. An X scanner 117-1 (first observation scanning unit) and a Y scanner 117-2 (second observation scanning unit) which serve to scan the light emitted from the light source 115 for fundus observation on the fundus of the eye 100 (function as observation scanning units) are disposed on the optical path L2. The lens 101-2 (third lens) is disposed such that its focal position is located near the central position between the X scanner 117-1 and the Y scanner 117-2. The X scanner 117-1 is formed from a polygon mirror to scan in the X direction at high speed. The X scanner 117-1 may be formed from a resonance mirror. A single detector 116 is formed from an APD (avalanche photodiode), and detects light scattered/reflected by the fundus. A prism 118 is a prism on which a perforated mirror or hollow mirror is deposited, and separates illumination light emitted from a light source 115 and return light from the fundus.

Figure 6:
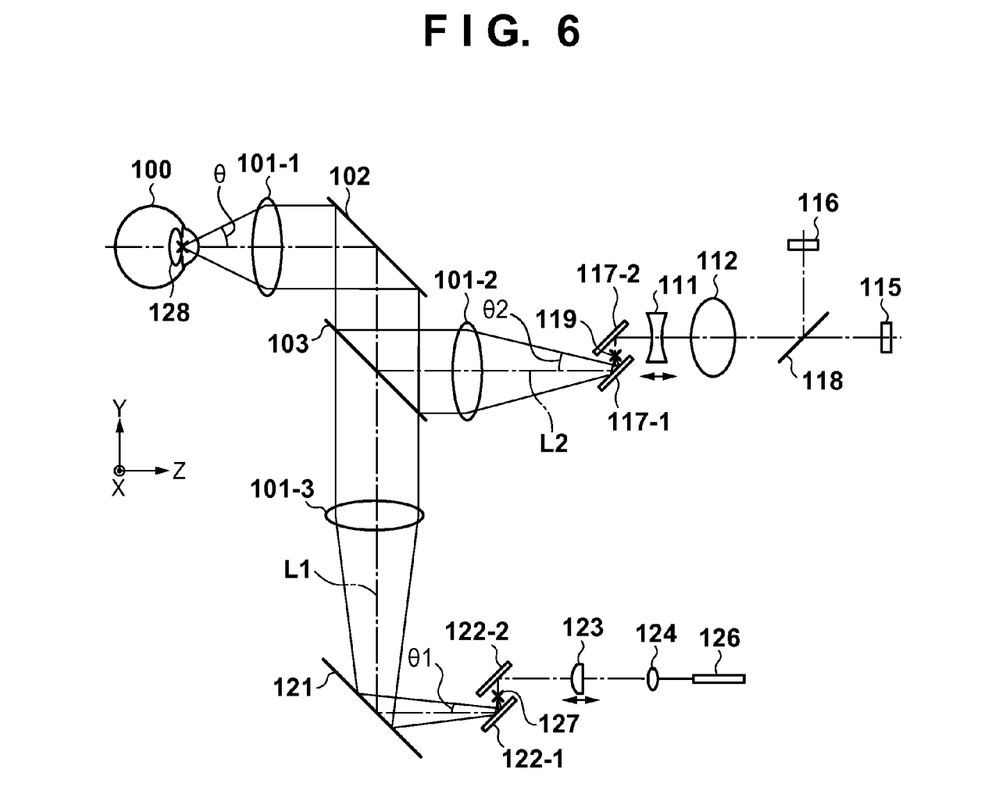
FIG. 6 is a view showing a pupil light beam in the optical coherence tomographic apparatus according to the second embodiment.

FIG. 6 shows the conjugate relationship between the pupil position and the optical paths L1 and L2, and a light beam from the pupil. The optical path L1 is the same as that in the first embodiment, and hence a description of it will be omitted. On the optical path L2, a scanner central position 119 between the X scanner 117-1 and the Y scanner 117-2 is conjugate to a pupil position 128 of the eye 100. The lens 101-2 and the scanner central position 119 (between the X scanner 117-1 and the Y scanner 117-2) are disposed to make a light beam almost parallel between a lens 101-1 and the lens 101-2. According to this arrangement, an optical path with a measurement light deflecting unit serving as an object point becomes almost parallel between the lens 101-1 and the lens 101-2. This can make the incident angle of light on a first dichroic mirror 102 coincide with that on a second dichroic mirror 103, even when the X scanner 177-1 and the Y scanner 117-2 perform scanning.

The optical path L1 and the optical path L2 are formed so as to share the lens 101-1. The lens 101-2 and the lens 101-3 are formed from lenses having the same size and made of the same material. This allows to use the same optical systems up to the X and Y scanners on the optical paths L1 and L2 from the eye 100, and hence can unify optical characteristics on the two optical paths.

In this case, as shown in FIG. 6, let θ be the spread angle of a light beam from the pupil of the eye 100 relative to the pupil, θ1 be the spread angle of a light beam from the pupil relative to a scanner central position 127, and θ2 be the spread angle of a light beam from the pupil relative to the scanner central position 119. That is, assume that the scanners provide the angles θ1 and θ2 to light beams to obtain the spread angle θ of a light beam from the pupil on the two optical paths L1 and L2.

In addition, it is possible to unify, as one of optical characteristics, the optical magnification at the scanner central position 119 relative to a pupil position 128 and the optical magnification of the scanner central position 127 relative to the pupil position 128 on both the optical paths. As a result, it is possible to unify the relationships between the scan angles of the X and Y scanners on the respective optical paths and the irradiation positions on the fundus of the eye 100 on both the optical paths. This can set θ1=θ2. This makes it possible to reduce the error between the respective scan positions.

As has been described above, according to this embodiment, in the optical coherence tomographic apparatus, making the incident angles of beams on the dichroic mirrors constant can improve the wavelength separation accuracy. In addition, disposing the focus lens between the irradiation light source on the fiber end and the XY scanner can simplify the driving mechanism. Furthermore, since there is no need to move the irradiation light source, it is possible to provide an optical coherence tomographic apparatus which can keep a polarization state. Moreover, using the same lens on the measurement optical path and fundus observation optical path of the OCT can reduce measurement errors.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-014582 filed on Jan. 26, 2012, which is hereby incorporated by reference herein in its entirety.

What is claimed is:

1. An optical coherence tomographic apparatus which obtains a tomographic image of an object based on light obtained by combining return light from the object irradiated with measurement light through a first lens and reference light corresponding to the measurement light, the apparatus comprising:
   a scanning unit configured to be provided on an optical path of the measurement light and configured to scan the measurement light on the object;
   a second lens configured to be disposed between said scanning unit and the object on the optical path of the measurement light;
   an optical path branching unit configured to be disposed between the first lens and said second lens and configured to make the optical path of the measurement light branch off to an observation optical path for observation of the object,
   wherein the first lens is an objective lens,
   wherein said second lens and said scanning unit are disposed so as to make a plurality of light beams, obtained by said scanning unit scanning the measurement light between the objective lens and said second lens, become almost parallel to each other and such that the plurality of light beams obtained by said scanning unit irradiate the objective lens almost in parallel.

2. The apparatus according to claim 1, wherein said scanning unit includes a first scanning unit configured to scan the measurement light on the object in a first direction, and a second scanning unit configured to scan the measurement light in a second direction intersecting the first direction, and
   wherein a position conjugate to a predetermined region of the object is disposed between said first scanning unit and said second scanning unit.

3. The apparatus according to claim 2, wherein said second lens and said first and second scanning units are disposed such that a position between said first and second scanning units is conjugate with respect to an anterior ocular segment of the eye.

4. The apparatus according to claim 3,
   wherein the object is an eye,
   wherein the observation optical path is a first observation optical path,
   the apparatus further comprising:
   a fundus observation optical system which is disposed on the first observation optical path and is for observing a fundus of the eye;
   a second optical path branching unit configured to be disposed between the first lens and the second lens and configured to make the optical path of the measurement light branch off to a second observation optical path; and
   an anterior ocular segment observation optical system which is disposed on the second observation optical path and is for observing an anterior ocular segment of the eye.

5. The apparatus according to claim 3, further comprising:
third and fourth scanning units which are disposed on the observation optical path and are configured to scan the measurement light onto the fundus of the eye in directions crossing each other; and
a third lens which is disposed on the observation optical path and is disposed between said third and fourth scanning units and said optical path branching unit,
wherein said third lens and said third and fourth scanning units are disposed such that a position between said third and fourth scanning units is conjugate with respect to the anterior ocular segment.

6. The apparatus according to claim 5, wherein the shape and material of said third lens is the same as the shape and material of said second lens.

7. The apparatus according to claim 1, wherein the first lens, said second lens, and said scanning unit are disposed so as to make light almost parallel on the optical path of the measurement light between the first lens and said second lens.

8. The apparatus according to claim 7, further comprising:
an observation scanning unit configured to scan observation light emitted from an observation light source on the object; and
a third lens disposed between said observation scanning unit and the object on the observation optical path.

9. The apparatus according to claim 8, wherein said observation scanning unit comprises a first observation scanning unit configured to scan the observation light on the object in a first direction, and a second scanning unit configured to scan the observation light in a second direction intersecting the first direction, and
wherein a position conjugate to a predetermined region of the object is disposed between said first observation scanning unit and said second observation scanning unit.

10. The apparatus according to claim 8, wherein the first lens, said third lens, and said observation scanning unit are disposed so as to make light almost parallel on the optical path of the observation light between the first lens and said third lens.

11. The apparatus according to claim 8, wherein the shape and material of said third lens is the same as the shape and material of said second lens.

12. The apparatus according to claim 1, further comprising:
a dividing unit configured to split light emitted from a light source into the measurement light and the reference light; and
a focus lens configured to be disposed between said dividing unit and said scanning unit on the optical path of the measurement light.

13. The apparatus according to claim 12, further comprising a fiber disposed on the optical path of the measurement light,
wherein said dividing unit comprises an optical coupler connected to said fiber, and
wherein said focus lens is disposed between an end of said fiber and said scanning unit.

14. The apparatus according to claim 12, further comprising a driving unit configured to drive said focus lens along the optical path of the measurement light.

15. The apparatus according to claim 1, wherein the observation optical path is disposed on a reflection optical path of said optical path branching unit, and
wherein the optical path of the measurement light is disposed on a transmission optical path of said optical path branching unit.

16. The apparatus according to claim 1, wherein the optical path branching unit is a first optical path branching unit,
wherein the observation optical path is first observation optical path,
wherein the apparatus further comprises a second optical path branching unit configured to be disposed between the first lens and said second lens and configured to make the optical path of the measurement light branch off to an second observation optical path for observation of the object,
wherein the second optical path branching unit is different from the first optical path branching unit,
wherein the second observation optical path is different from the first observation optical path,
wherein said second lens and said scanning unit are disposed so as to make the plurality of light beams become almost parallel to each other so as to make the incident angle of light on the first optical path branching unit coincide with that on the second optical path branching unit.

17. The apparatus according to claim 1, wherein the optical path branching unit is a first optical path branching unit,
wherein the observation optical path is first observation optical path,
wherein the apparatus further comprises a second optical path branching unit configured to be disposed between the first lens and said second lens and configured to make the optical path of the measurement light branch off to a second observation optical path for observation of the object,
wherein the second optical path branching unit is different from the first optical path branching unit,
wherein the second observation optical path is different from the first observation optical path,
wherein said second lens and said scanning unit are disposed so as to make the incident angles of the plurality of light beams on the optical path branching units become almost the same angle.

18. The apparatus according to claim 1, wherein said second lens and said scanning unit are disposed so as to make the plurality of light beams become parallel to each other and such that the plurality of light beams obtained by said scanning unit irradiate the objective lens in parallel.

19. The apparatus according to claim 1, wherein said second lens and said scanning unit are disposed such that the plurality of light beams obtained by said scanning unit irradiate the objective lens in parallel.

20. An optical coherence tomographic apparatus which includes an optical path branching unit configured to make an optical path of measurement light branch off to an observation optical path for observation of an object, and configured to obtain a tomographic image of the object based on light obtained by combining return light from the object irradiated with the measurement light from the optical path branching unit through a first lens and reference light corresponding to the measurement light, the apparatus comprising:
a scanning unit configured to be provided on an optical path of the measurement light and configured to scan the measurement light on the object; and
a second lens disposed on the optical path of the measurement light so as to make a plurality of light beams, obtained by said scanning unit scanning the measurement light on the optical path branching unit, become almost parallel to each other,
wherein the first lens is an objective lens, wherein said second lens and said scanning unit are disposed such that the plurality of light beams obtained by said scanning unit irradiate the objective lens almost in parallel.

21. The apparatus according to claim 20, further comprising a dividing unit configured to split light from a light source into the measurement light and the reference light.

22. The apparatus according to claim 20, wherein the observation optical path is disposed on a reflection optical path of said optical path branching unit, and wherein the optical path of the measurement light is disposed on a transmission optical path of said optical path branching unit.

23. An optical coherence tomographic apparatus which obtains a tomographic image of an eye based on light obtained by combining return light from the eye irradiated with measurement light through a first lens and reference light corresponding to the measurement light, the apparatus comprising:

a scanning unit configured to be provided on an optical path of the measurement light and configured to scan the measurement light on the eye;

a second lens configured to be disposed between said scanning unit and the first lens on the optical path of the measurement light;

wherein the first lens is an objective lens;

wherein said second lens and said scanning unit are disposed such that the incident angles of a plurality of light beams obtained by said scanning unit on the objective lens become almost the same angle, the plurality of light beams being obtained by said scanning unit scanning the measurement light between the objective lens and said second lens;

a first optical path branching unit configured to be disposed between the first lens and said second lens and configured to make the optical path of the measurement light branch off to a first observation optical path for observation of the eye;

a second optical path branching unit configured to be disposed between the first lens and the second lens and configured to make the optical path of the measurement light branch off to a second observation optical path; and an anterior ocular segment observation optical system which is disposed on the second observation optical path and is for observing an anterior ocular segment of the eye, wherein the first observation optical path is disposed on a reflection optical path of said first optical path branching unit, wherein the second observation optical path is disposed on a transmission optical path of said second optical path branching unit, and wherein the optical path of the measurement light is disposed on a transmission optical path of said first optical path branching unit and a reflection optical path of said second optical path branching unit.

24. The apparatus according to claim 23, wherein the first lens is an objective lens, wherein said second lens and said scanning unit are disposed so as to make the incident angles of a plurality of light beams on the first and second optical path branching units become almost the same angle.

* * * * *